United States Patent [19]

Furukawa et al.

[11] 4,023,276

[45] May 17, 1977

[54] DIAGNOSTIC SCALE FOR INTERPRETATION OF ELECTROCARDIOGRAM

[75] Inventors: Toshiyuki Furukawa, Takarazuka; Toshio Kato, Osaka, both of Japan

[73] Assignee: Yamanouchi Pharmaceutical Co., Ltd., Tokyo, Japan

[22] Filed: Dec. 22, 1975

[21] Appl. No.: 643,102

[30] Foreign Application Priority Data

Dec. 28, 1974 Japan .................. 50-4243[U]

[52] U.S. Cl. .................. 33/1 C; 33/1 SB; 35/17; 116/135; 128/2.06 R
[51] Int. Cl.² .................. G09F 9/00; A61B 5/02
[58] Field of Search .................. 33/1 C, 1 SB, 1 SD; 35/17; 116/114 AJ, 130, 131, 135; 128/2.05 R, 2.06 R, 2.06 V; 235/89 R

[56] References Cited

UNITED STATES PATENTS

| 2,248,162 | 7/1941 | Araujo | 35/17 |
| 2,876,764 | 3/1959 | Guttner et al. | 116/135 |
| 3,884,221 | 5/1975 | Eastman | 128/2.06 V |

FOREIGN PATENTS OR APPLICATIONS

| 187,459 | 10/1921 | United Kingdom | 116/135 |
| 525,391 | 8/1940 | United Kingdom | 116/135 |

Primary Examiner—Richard E. Aegerter
Assistant Examiner—Richard R. Stearns
Attorney, Agent, or Firm—Burgess Ryan and Wayne

[57] ABSTRACT

A diagnostic scale for interpretation of an electrocardiogram composed of a fixed diagnostic scale having formed two sections on the surface thereof, one section displays the interrogation items concerning various parameters of the electrocardiogram, and another the diagnostic names of the electrocardiogram; and sliding scales each indicating the affirmation or denial to each of the interrogation items above described. By arranging the sliding scales according to the affirmation or denial to each interrogation item relative to a electrocardiogram of a patient, diagnostic names of the electrocardiogram of the patient can be quickly and objectively displayed on the fixed diagnostic scale by the mark formed by the arranged scales.

4 Claims, 5 Drawing Figures

DIAGNOSTIC SCALE FOR INTERPRETATION OF ELECTROCARDIOGRAM

DETAILED EXPLANATION OF THE INVENTION

The present invention relates to a diagnostic scale for interpretation of an electrocardiogram and more particularly it relates to a diagnostic scale for interpretation of an electrocardiogram capable of ascertaining the diagnostic names objectively and quickly from the information read from the electrocardiogram of a patient.

In general, the correct analysis and diagnosis of an electrocardiogram require a long training and experience. Furthermore, the diagnostic result from the same electrocardiogram differs according to the persons observing it owing to the indistinct nature of the diagnostic criteria.

An object of this invention is, therefore, to provide an improved diagnostic scale for interpretation of an electrocardiogram capable of ascertaining objectively and quickly diagnostic names of a patient based on the information read from his electrocardiogram.

The aforesaid object of this invention can be attained by the present invention. That is, according to the invention, there is provided with a diagnostic scale for interpretation of an electrocardiogram composed of a combination of a fixed diagnostic scale having two sections which displays the interrogation items concerning various parameters of the electrocardiogram and the diagnostic names of the electrocardiogram respectively and the sliding scales each indicating the affirmation or denial for each interrogation item. By arranging the sliding scales according to the affirmation or denial of each interrogation item relative to an electrocardiogram of a patient, diagnostic names of the electrocardiogram can be quickly and objectively displayed on the fixed diagnostic scale by the mark formed by the arranged scales.

Now, the diagnostic scale for interpretation of an electrocardiogram will be explained by referring to the embodiments shown in the accompanying drawings.

Figure 1:
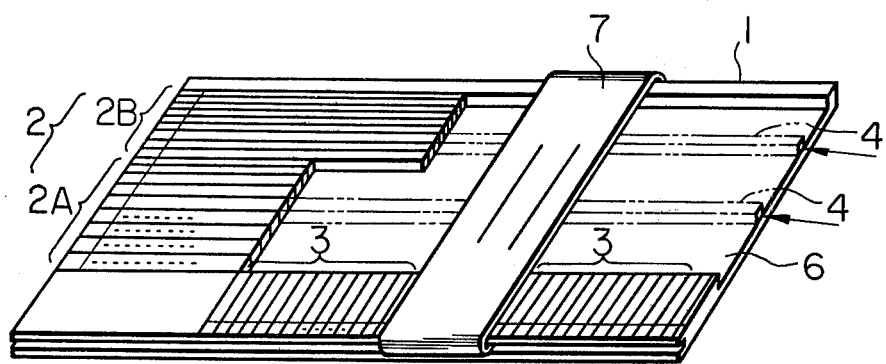
FIG. 1 is a perspective view of an embodiment of the diagnostic scale for interpretation of an electrocardiogram of this invention.

In FIG. 1 which shows a fundamental embodiment of the diagnostic scale for interpretation of an electrocardiogram of this invention, a rectangular fixed diagnostic scale 1 has at the left side thereof (in the state shown in the figure) a section 2 displaying the interrogation items concerning the diagnostic criteria. In the embodiment shown in FIG. 1, the section 2 is marked off into a subsection 2A for analyzing of wave form and a subsection 2B for analyzing of arrhythmia.

Figure 3:
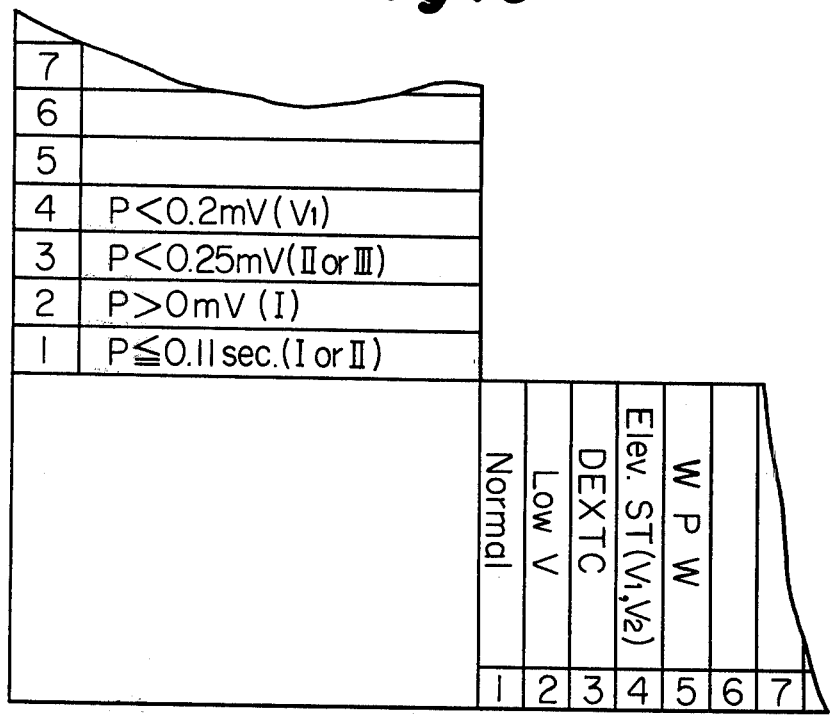
FIG. 3 is an elevated partial plane view of the diagnostic scale illustrated in FIG. 1.

As shown in FIG. 3 of the accompanying drawings, the columns of the subsection 2A for analyzing of wave form display the following terms from the bottom to the top:

1. "Is the width of P-wave in lead I or lead II shorter than 0.11 second?",
2. "Is P-wave positive in lead I?",
3. "Is the height of P-wave in lead II or lead III less than 0.25 mV?",
4. "Is the height of P-wave in lead $V_1$ less than 0.25 mV?"

Also, the columns of the subsection 2B for arrhythmia display, for example, the following terms (not shown in figures);

"Is QRS-wave observed?",
"Are R—R intervals regular?"

In addition, the kinds and the number of the interrogation items used in this invention are not limited to those shown above and they may be modified as the occasion demands.

On the other hand, the diagnostic scale 1 has at the lower portion thereof a section 3 displaying the indications of the diagnostic names of an electrocardiogram corresponding to the interrogation items described n the subsection 2A and subsection 2B. That is, the section 3 display the following diagnostic names as shown in FIG. 3;

1. "Normal",
2. "Low Voltage",
3. "Hypertrophy of Right Ventricle (DEXTC)",
4. "ST Elevation in $V_1$ and $V_2$",
5. "WPW Syndrome".

Figure 2:
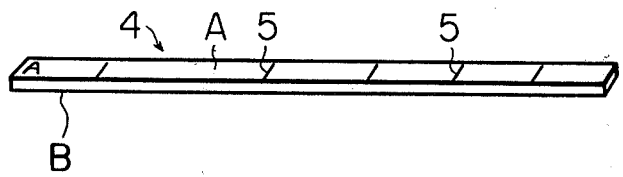
FIG. 2 is an elevated perspective view of the sliding scale used for diagnostic scale of this invention illustrated in FIG. 1.

The fixed diagnostic scale 1 of this invention is so constructed that each of sliding scales 4 as shown in FIG. 2 in the number corresponding to the number of the interrogation displayed in the section 2 can be inserted in the diagnostic scale at the rightward extension line of the corresponding interrogation item in the section 2. Each of the sliding scales 4 has a face A indicating "affirmation" or "yes" for each interrogation and a face B (the opposite side) indicating "denial" or "no" to each interrogation. Also, a mark 5 is formed beforehand on the faces A and B of the scale 4 at the position on the extension line of the diagnositc names those the interrogation displayed in section 2 concerns and in this case it is preferred that if the color of the mark 5 on the "affirmation" face of the sliding scale is black, the color of the mark on the "denial" face of the sliding scale is red. That is, if there is the term indicating a diagnostic name in the section 3, which is affirmative for a interrogation of, for example, "Is the width of P-wave in lead I or lead II less than 0.11 second?", in the section 2, a black mark 5 is formed on the "affirmation" face of the sliding scale corresponding to the interrogation item at the position on the extension line of the diagnostic name in the section 3 and also a red mark 5 is formed on the "denial" face of the sliding scale at the position corresponding to the black mark 5 on the opposite side.

Thus, if there are many diagnostic names indicated in the section 3, which are affirmative for a specific interrogation item in the section 2, there are also many marks 5 on the face A and the face B of the slide 4 corresponding to the specific interrogation item, while if the number of the diagnostic name affirmative for a specific interrogation item is less, the number of the marks formed on the faces of the sliding scale is also less.

In use, the sliding scales 4 are arranged in the recessed portion 6 of the fixed diagnostic scale 1 in such a manner that when the result read from the electrocardiogram of a patient is affirmative for a specific interrogation item displayed in the section 2, the sliding scale corresponding to the interrogation item is arranged with the face A up, while when the result is not affirmative, the sliding scale is arranged with the face B up. Thus, the whole interrogation item displayed in the section 2 (i.e., the whole number of the sliding scales) are checked and the whole sliding scales are arranged in the manner as described above. In this case, if all black marks 5 of the pre-determined number of the sliding scales are in a line at the direction perpendicular to the sliding scale, the diagnostic names in the section 3 indicated by the black line are the diagnostic names of the electrocardiogram of the patient. Te positions of the marks 5 may be observed by the naked eye but the observation can be made more correctly using a cursor.

That is, as shown in FIG. 1, a cursor 7 is mounted on the fixed diagnostic scale 1 slidably along the lengthwise direction and the cursor can be moved for observing the line of marks 5.

Figure 4:
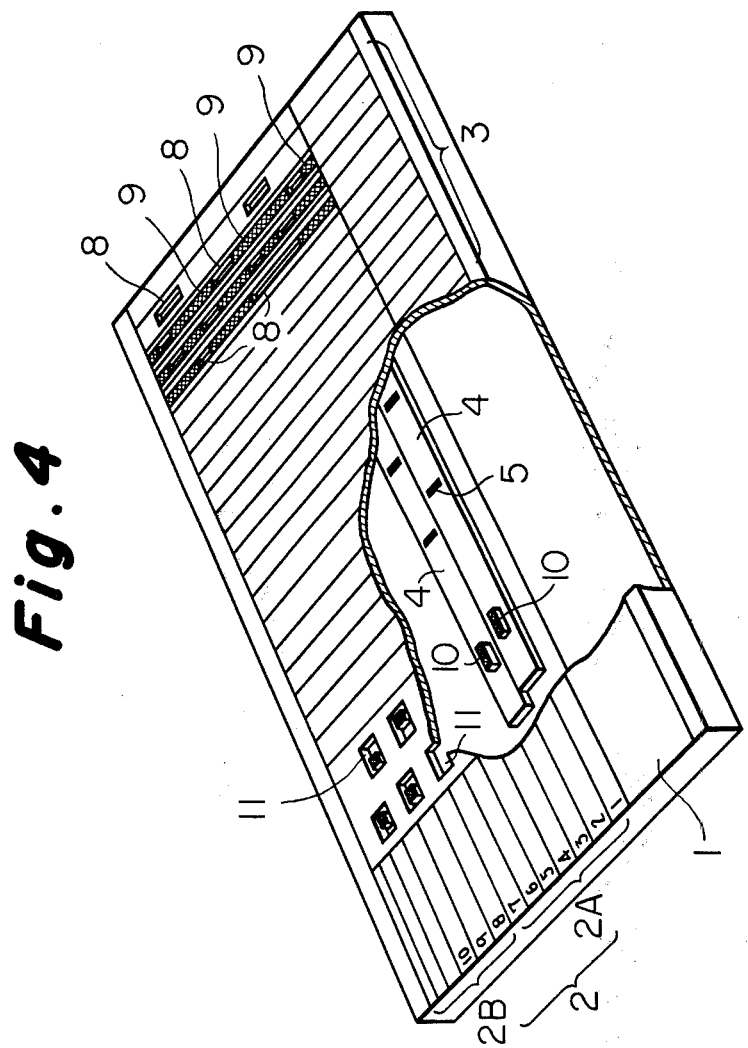
FIG. 4 is a perspective view of another embodiment of the diagnostic scale for interpretation of electrocardiogram of this invention.
Figure 5:
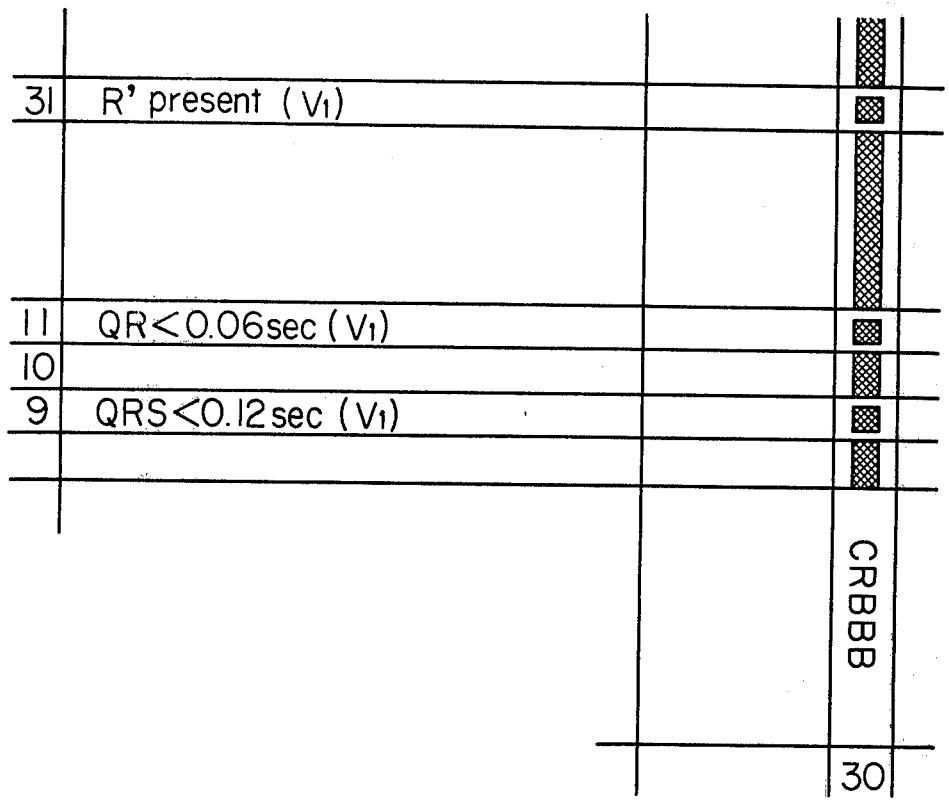
FIG. 5 is a view showing an example of using the diagnostic scale of this invention.

Then, another embodiment of the diagnostic scale for interpretation of electrocardiogram of this invention will further be explained by referring to FIG. 4 and FIG. 5 of the accompanying drawings. In the embodiment shown in the figures, the operation of selecting the face A and face B of each sliding scale as described in the aforesaid example is unnecessary. That is, as shown in FIG. 4, the "of affirmation" or "denial" to each interrogation item can be indicated by only moving each slide 4 between the two positions of "affirmation" and "denial".

That is, as shown in FIG. 4, a fixed diagnostic scale 1 is an envelope type scale having a hollow space therein and a section 2 displaying the interrogation items for electrocardiograms of patients and a section 3 displaying the indications of the diagnostic names are formed on the surface of the diagnostic scale as in the aforesaid example. The section 2 is also marked off into a subsection 2A and subsection 2B. Furthermore, a number of slits or openings 8, 8, 8, are formed in the surface or the panel of the diagnostic scale 1 at the definite positions. The position of each slit 8 is one where the extension line of a specific interrogation item in the section 2 crosses with the extension line of the diagnostic name in the section 3 which the interrogation concerns, which corresponds to the position of the mark 5 as in the above illustrated example. Also, the cross positions where the diagnostic names have no relation to the interrogation, such as the positions 9, 9, form an unbroken surface and each of such positions may be marked in black color between the slit 8 and slit 8 (the positions are shown by cross hatches). Thus, in the insides of the slits 8, 8, formed on the extension line of the specific diagnostic name are marked by black color, the diagnostic name in the section 3 is indicated by the continuous black mark.

On the other hand, in the hollow space of the fixed diagnostic scale 1 are placed slidably strip-like scales 4, 4, each corresponding to each interrogation item in the section 2. In FIG. 4, only two such sliding scales are shown for connvenience's sake but in fact all of sliding scales corresponding to all of the interrogation items in the section 2 are inserted in the space. Furthermore, each sliding scale 4 has mark 5 or marks 5, 5, on the upperface of it as the face A in the abovedescribed example. In this case, the mark 5 is shown by black color only when the position of the mark indicates "affirmation" for the interrogation and other portion is left in the ground color or white.

Moreover, a small projection or knob 10 is formed on each slide 4 at the position near the left-hand side thereof, the knob 10 is extruded upwardly through an opening 11 formed in the panel of the diagnostic scale 1, and the sliding scale 4 can be moved selectively to the "affirmation" or a "denial" position by moving the knob 10 in the opening 11. Thus, if the result of the electrocardiogram is affirmative for a specific interrogation item displayed in the section 2, the knob 10 of the corresponding sliding scale is moved to the "affirmation" position, whereby the insides of the slits 8, 8, in the panel of the scale 1 positioned on the sliding scale are shown by black color.

Thus, if, for example, the results of electrocardiogram of a patient are affirmative for the following interrogation among the interrogation items displayed in the section 2;

9. "Is the width of QRS wave in lead $V_1$ less than 0.12 second?",

11. "Is the QR duration in lead $V_1$ less than 0.06 second?", and

31. "Is R'-wave absent in lead $V_1$ ?", the extension line of the diagnostic name 30) "Complete right bundle branch block (CRBBB)" in the section 3 becomes a continuous black line.

Thus, the electrocardiographic diagnosis of the patient is "complete right bundle branch block".

As mentioned above, according to the diagnostic scale for interpretation of electrocardiogram of this invention, the diagnostic names of electrocardiogram of a patient can be determined by simply checking each interrogation by each sliding scale corresponding to the interrogation item based on the result of electrocardiogram and thus the diagnostic name of the electrocardiogram of a patient can be objectively and quickly determined different from a conventional subjective decision by a person performing the electrocardiogram.

What is claimed is:

1. A diagnostic scale for interpretation of electrocardiograms comprising in combination, a fixed substantially rectangular diagnostic scale having a first section arranged along the width of said fixed scale and indicating various interrogation items concerning an electrocardiogram and a second section arranged along the length of said fixed scale and indicating the diagnostic names presumed from the combination of several of these interrogation items, and a plurality of elongated sliding scales each displaceable to distinct positions aligned with the length of said fixed scale and indicating the affirmation or denial to each symptom in the aforesaid interrogation and each having at least one mark aligned with at least one of said diagnostic names in said affirmation position, the alignment of a group of said marks indicating said diagnosis corresponding to said one of said diagnostic names.

2. The diagnostic scale for interpretation of electrocardiograms as claimed in claim 1 wherein each said sliding scale has formed on one face a first set of said marks indicating the affirmation for the interrogation displayed in the first section at positions corresponding to said diagnostic names indicated in the second section, and wherein said sliding scale has formed on the opposite face a second set of marks indicating the denial to the interrogation at the positions corresponding to the affirmation positions.

3. The diagnostic scale for interpretation of electrocardiograms as claimed in claim 2 wherein each affirmation mark is marked by black color and each denial mark is marked by red color.

4. The diagnostic scale for interpretation of electrocardiograms as claimed in claim 1 further including a panel on said fixed diagnostic scale having formed therein slits at positions corresponding to the affirmation for each interrogation displayed in the first section which is related to a diagnostic name in said second section and also an opening formed over each sliding scale in the area of said panel to the left of said second section, each of said sliding scales having formed thereon marks corresponding to the affirmation of each interrogation, and a knob formed near the left hand side thereof for moving the sliding scale through said opening for selectively positioning the sliding scales in either an affirmative or denial position.

* * * * *

UNITED STATES PATENT OFFICE
CERTIFICATE OF CORRECTION

Patent No. 4,023,276  Dated May 17, 1977

Inventor(s) Toshiyuki Furukawa, et al

It is certified that error appears in the above-identified patent and that said Letters Patent are hereby corrected as shown below:

On the Title Page, under "Inventors" and particularly their addresses: Change the address of Mr. Furukawa from "Takarazuka" to --Hyogo--.

Column 2, line 22: Change "n" to --in--.

Column 2, line 42: Change "diagnositc" to --diagnostic--.

Column 3, line 15: Change "Te" to --The--.

Column 3, line 29: Change '"of affirmation"' to --"affirmation"--.

Column 3, line 62: After "of" insert --the--.

Signed and Sealed this

Twenty-ninth Day of November 197

[SEAL]

Attest:

RUTH C. MASON  
Attesting Officer

LUTRELLE F. PARKER  
Acting Commissioner of Patents and Trademark